United States Patent
Pittman

(10) Patent No.: US 6,860,894 B1
(45) Date of Patent: Mar. 1, 2005

(54) LAPAROSCOPIC LIFTER APPARATUS AND METHOD

(76) Inventor: Gregory R. Pittman, 5101 E. 79$^{th}$ St., Tulsa, OK (US) 74136

( * ) Notice: Subject to any disclaimer, the term of this patent is extended or adjusted under 35 U.S.C. 154(b) by 381 days.

(21) Appl. No.: 10/075,948

(22) Filed: Feb. 15, 2002

(51) Int. Cl.$^{7}$ .............................................. A61B 17/28
(52) U.S. Cl. ........................ 606/205; 606/206; 606/113
(58) Field of Search ................. 606/205–211, 113–114, 606/127, 108

(56) References Cited

U.S. PATENT DOCUMENTS 4,174,715 A  * 11/1979 Hasson ...................... 606/206

* cited by examiner

Primary Examiner—Kevin T. Truong
Assistant Examiner—(Jackie) Tan-Uyen T. Ho
(74) Attorney, Agent, or Firm—Barbara R. Greenberg

(57) ABSTRACT

A surgical instrument, mainly a laparoscopic organ lifter apparatus and method comprising a flexible arm component having a first manipulating bilateral handle with a central element securing a solid rod terminating in a connector piece holding flexible arms, the solid rod passing through an internally threaded ring housing a locking screw and a tubular rod component having a hollow rod with a proximal hollow externally threaded coupler disposed to receive the internally threaded ring when the hollow rod houses the flexible arms component. To lift and hold an organ, an operator thrusts the first bilateral handle toward the hollow rod proximal end thereby extending the flexible arms outside a hollow tube distal end where the arms assume an arcuate shape appropriate to lift and hold steady an organ such as a spleen.

12 Claims, 3 Drawing Sheets

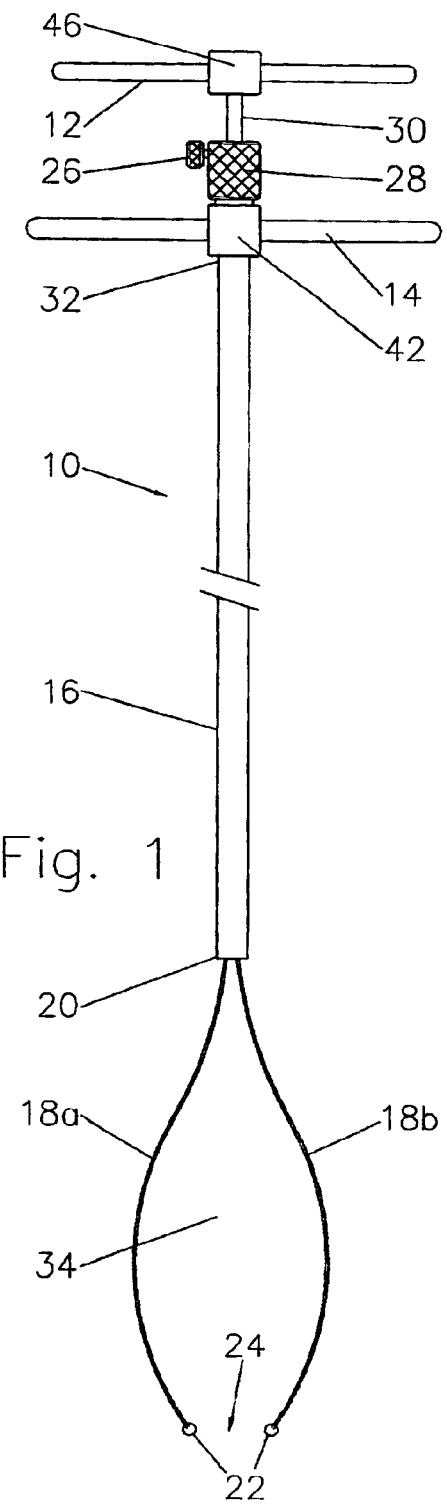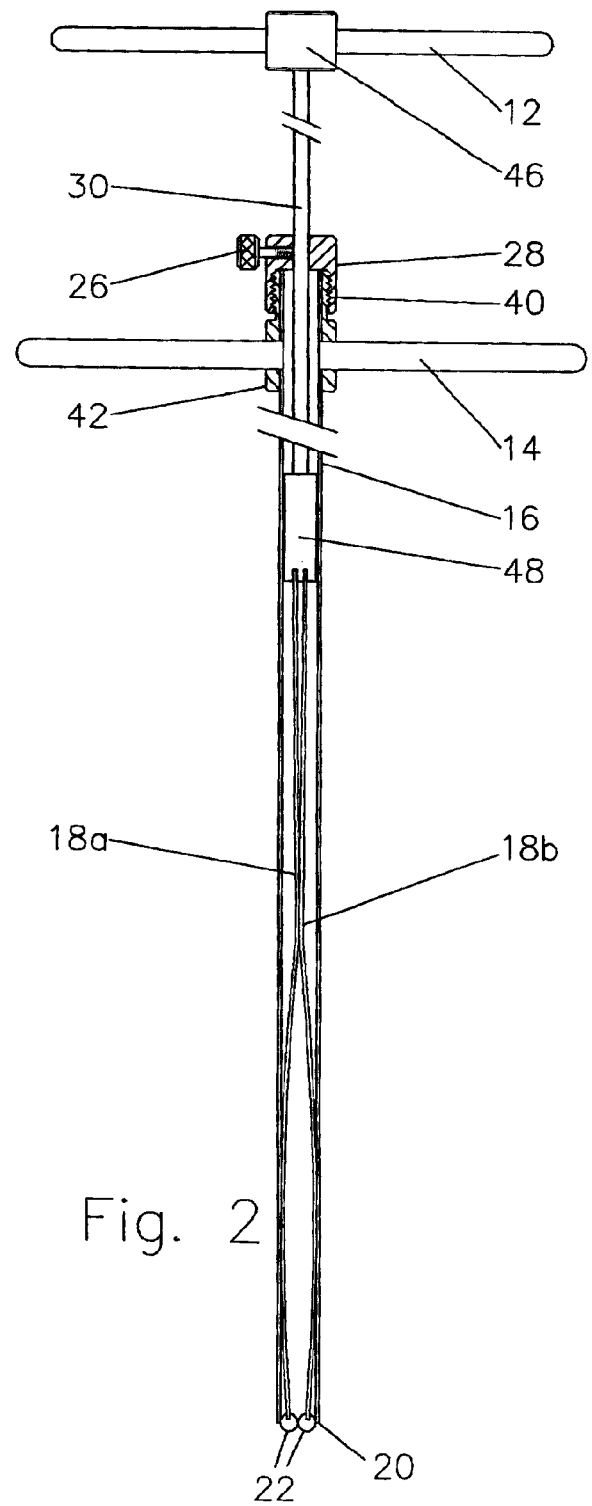

LAPAROSCOPIC LIFTER APPARATUS AND METHOD

BACKGROUND OF THE INVENTION

1. Field of the Invention

The present invention relates to surgical instruments for use during laparoscopic surgery. More particularly, the invention is directed to a surgical tool designed to gently manipulate and lift an organ thereby providing a means for allowing safe organ release from body cavity constraints and then, expedient organ removal.

2. Description of the Prior Art

In order to perform laparoscopic surgery, surgical instruments are inserted through discrete openings in a patient's abdominal cavity eliminating a need for lengthy incisions accompanied by excess patient trauma and surgical complications. Most laparoscopic surgical instruments are designed to grasp tissue in opposing rough surfaced contact jaws terminating in irregular shapes not useful for organ manipulation and having the potential to cause organ perforation.

In U.S. Pat. No. 6,013,095, an endoscopic grasping tool has grasping pieces with tip end portions formed into inwardly bent beak like shapes designed to engage each other and grasp a foreign material.

U.S. Pat. No. 5,222,973 teaches a laparoscopic grasping tool with either forceps type jaws or hemostat type jaws, the jaws having serrated contact surfaces for a continuous jaw closure and increased grasping force in order to grasp tissue pedicles and other body structures.

U.S. Pat. No. 4,944,741 defines a laparoscopic surgical instrument having pivotal plate like jaws that selectively move toward and away from each other and are used to grasp vessels, tubes or stents during a laparoscopic procedure.

The above described inventions are not designed primarily for organ lifting and, therefore, have serious limitations when organ lifting is a primary concern. Teeth, projections or ridges on grasping surfaces present obvious organ perforation hazards when instrument and organ contact occurs. The focus is on grasping and not on lifting.

The present invention is a laparoscopic surgical instrument designed to assist with laparoscopic surgical removal of organs, more specifically solid organs within a patient's abdominal cavity, in a simple and novel manner. The device has arms that are carefully and precisely extended and manipulated to gently lift, position and hold an organ, such as a spleen, so that necessary surgical procedures regarding the organ can be safely performed.

SUMMARY OF THE INVENTION

A principal objective of the present invention is to provide a surgical instrument to assist in organ removal by providing a simple, useful and unique means for cleanly lifting and securely holding an organ during a laparoscopic surgical procedure.

Another principal objective of the present invention is to provide a laparoscopic surgical instrument that greatly benefits the removal of solid organs, such as a spleen or a kidney, having a narrow hilum where hilar dissection can be the most difficult part of a procedure.

Another objective of the present invention is to provide a laparoscopic lifting and holding instrument that can be manipulated to fit under an organ and gently lift the organ with minimal danger of organ damage and of subsequent operating field contamination.

Still another objective of the present invention is to markedly improve safety during laparoscopic procedures by decreasing operating time generally, and specifically by reducing the possibility of having to convert a laparoscopic procedure to an open procedure.

Yet, another objective of the present invention is to reduce surgical expenses by enhancing an operator's ability to do a procedure laparoscopically rather than through a large incision.

In brief, the present invention comprises a laparoscopic surgical instrument, mainly a laparoscopic lifter apparatus which includes a manipulating handle used to retract or eject flexible, band like arms having blunt ends into or out of a rigid tubular rod, the arms assuming opposing arcuate shapes upon ejection from the tubular rod and the arm's blunt ends separated by a gap so easy laparoscopic instrument placement for safe organ lifting can occur. With the band like arms retracted into the rigid tubular rod, the laparoscopic organ elevator is inserted into a patient's abdominal cavity through a trocar sleeve. Reaching an organ site, the arms are extended outside a tubular rod distal end to an optimal length depending on organ size and spring into preformed arcuate shapes defining an open ended oval contour, the open blunt ends positioned to allow arm encirclement of the organ. Then the instrument is manipulated to slip the arms underneath the organ where the organ can rest on the arms and be lifted and held securely by an operator using a second handle secured to the tubular rod. Now the organ hilum is exposed and blood vessels within the hilum can be safely dissected, ligated, sutured and clipped or stapled. After a surgical procedure is completed, since the laparoscopic lifter apparatus is an instrument assembled by inserting a first handle, solid rod, arm section into a second handle, tubular rod section, these sections can be easily separated, sterilized and reassembled for future use.

A laparoscopic surgical instrument in accordance with the present invention can be used to markedly improve the safety, costs, operating time and patient open conversion rate in laparoscopic organ removal procedures for a variety of organs such as a spleen, liver, kidney and a uterus.

BRIEF DESCRIPTION OF THE DRAWINGS

FIG. 1 is a plan view of an assembled laparoscopic lifter apparatus according to the present invention with arms associated therein shown in an extended, open position.

FIG. 2 is a longitudinal cross sectional view of an assembled laparoscopic lifter apparatus according to the present invention with arms associated therein shown in a retracted, closed position.

DETAILED DESCRIPTION OF THE DRAWINGS

Figure 3:
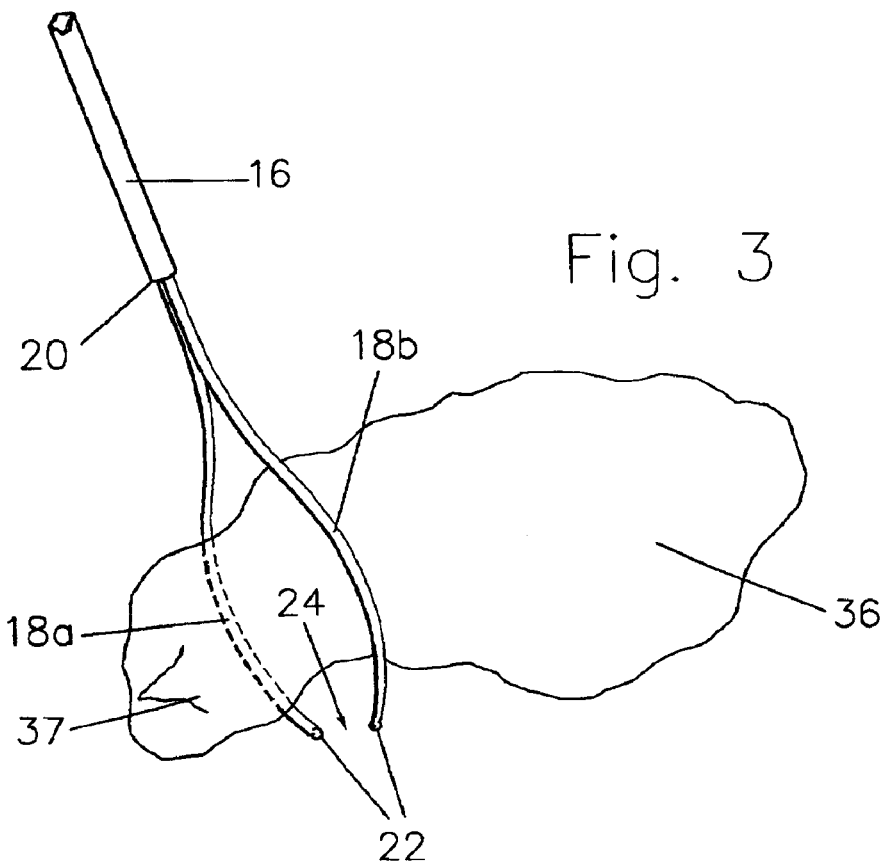
FIG. 3 is a perspective view of laparoscopic lifter apparatus arms according to the present invention commencing organ support.

Referring now to the drawings, FIG. 1 is a plan view of a surgical instrument, mainly an assembled laparoscopic organ lifter apparatus 10 comprising a first manipulating bilateral handle 12, a second holding and steadying bilateral handle 14, a strong, rigid tubular rod 16 housing more than one band like flexible arm 18a, 18b. Arms 18a, 18b exit tubular rod 16 at a distal end 20 and assume oppositely disposed preformed arcuate shapes. The band like arms 18a, 18b are mirror images of each other equal in length, width and depth, each arm 18a, 18b having a width substantially three to four times greater than the depth and each arm 18a, 18b ending in a blunt sphere 22, the blunt spheres 22 spaced apart to define an opening 24. Each arm 18a, 18b has a uniform width throughout its length. After arms 18a, 18b are extended to achieve a proper lifting position, a locking screw 26 retained in a threaded opening in an internally threaded ring 28 can be tightened to impinge on a solid rod 30 which is linked to arms 18a, 18b preventing arm up down movement and rotation. When locking screw 28 is loosened, arms 18a, 18b can be manipulated in unison a full 360 degrees by turning first handle 12 along a central axis. In addition, arms 18a, 18b can be retracted into the tubular rod 16 distal end 20 by an operator using first handle 12 to pull a solid rod 30 out of a tubular rod 16 proximal end 32 as illustrated in FIG. 2 showing a longitudinal cross sectional view of the assembled laparoscopic organ lifter 10.

Figure 4:
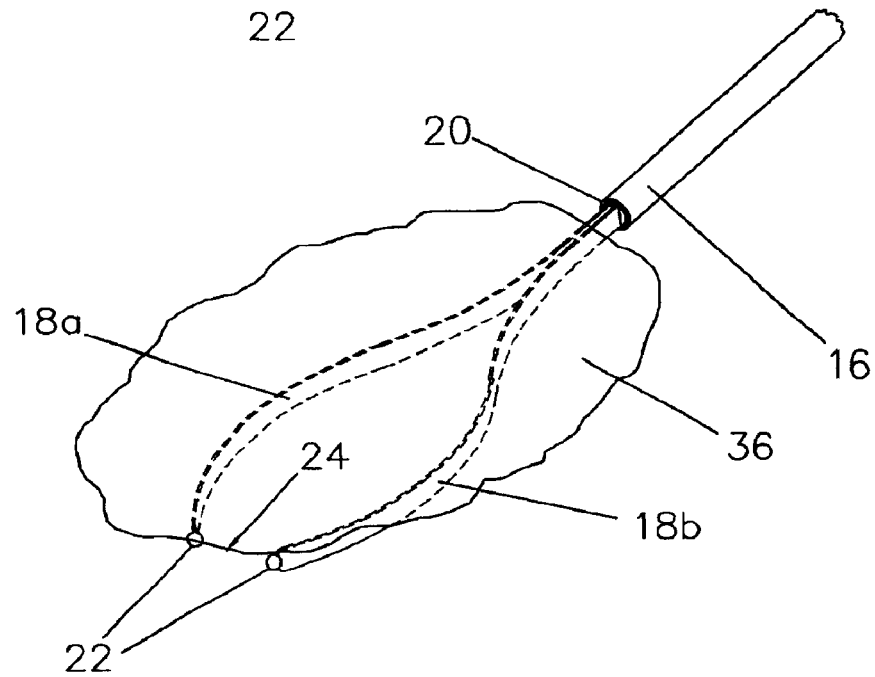
FIG. 4 is a perspective view of laparoscopic lifter apparatus arms according to the present invention supporting and lifting an organ.

When a surgical procedure requires organ elevation, the laparoscopic organ lifter apparatus 10 is initially positioned as illustrated in FIG. 2. The organ lifter apparatus 10 tubular rod 16 has an outer diameter so designed to fit through a small incision, 10 to 11 millimeters in length. In the case of a spleen removal, after the spleen is laterally resected, the organ lifter apparatus 10 with arms 18a, 18b retracted into tubular rod 20 as illustrated in FIG. 2 is inserted through the incision into an abdominal cavity. Next, an operator thrusts first handle 12 toward the tubular rod 16 proximal end 32 in order to slide solid rod 30 along with arms 18a, 18b through the tubular rod 16, so that arms 18a, 18b slowly eject from the tubular rod 16 distal end 20. As arms 18a, 18b are ejected, they gradually separate and assume arcuate shapes defining an open oval space 34, a maximum distance between the arms 18a, 18b increasing until full ejection occurs. At full ejection, blunt spheres 22 are separated by a distance of substantially 4 to 6 centimeters. The operator can stop the ejection at any point before full ejection to achieve optimal arms 18a, 18b ejected length and arcuate shape for lifting and holding organs of a variety of shapes and sizes. When optimal arms 11a, 18b ejection and positioning is achieved, locking screw 28 is tightened to impinge on rod 30 and the organ lifter apparatus 10 can lift and hold an organ so necessary surgical procedures can take place. Thus, the operator can slip the organ lifter apparatus 10 blunt spheres 22 opening 24 over an organ end, for example a spleen 36 end portion, and slide the organ lifter apparatus 10 with arms 18a, 18b around the spleen and then down and under the spleen 36, gently lifting the spleen 36 toward an anterior abdominal wall in order to expose the spleen 36 hilum 37 where blood vessels entering the spleen 36 can be safely dissected and sutured, ligated, clipped or stapled as shown in FIGS. 3 and 4. The spleen 36 rests on the thinnest or depth side of the extended arms 18a, 18b and is held by pressure induced friction force. An operator uses second handle 14 to steady the organ elevator 10 and first handle 12 to rotate, retract and extend arms 18a, 18b to an infinite number of positions finding a correct arms 18a, 18b opposing arcuate distance for optimum spleen 36 holding and lifting, the distance increasing as arms 18a, 18b are extended and decreasing as arms 18a, 18b are retracted.

Once the spleen 36 is divided from the hilum 37 and free from the abdominal cavity, the organ elevator 10 arms 18a, 18b are fully extended to achieve a maximum blunt sphere 22 opening 24 needed to slide the organ lifter apparatus 10 away from the spleen 36. At this point, arms 18a, 18b are retracted into rigid tubular rod 16, thereby diminishing the arms 18a, 18b arcuate shapes until finally arms 18a, 18b are fully enclosed in the tubular rod 16 and the blunt spheres 22 can be touching. At this time, the organ elevator 10 can be removed from the abdominal cavity.

The arms 18a, 18b have widths just slightly less than the rigid tubular rod 16 inner diameter which allows the rigid tubular rod 16 to act as a guide for arms 18a, 18b passing through tubular rod 16 and prevent arms 18a, 18b crossover during retraction while also providing a strong, unbendable lifting device during a lifting and holding procedure.

The tubular rod 16 can have an outside diameter of substantially 10 millimeters to fit into an 11 millimeter incision. Arms 18a, 18b, fully extended, can reach a distance of 12 to 18 centimeters when measured from the tubular rod 16 distal end 20 to arms 18a, 18b blunt spheres 22. If the organ lifter apparatus 10 is used to lift and hold a small organ such as a kidney, or a large organ such as a liver, an operator can retract or extend the arms 18a, 18b thereby changing this distance. Arms 18a, 18b have a width of substantially 6 to 8 millimeters and a depth of substantially 2 to 3 millimeters. The entire organ lifter apparatus 10 can be substantially 55 centimeters to 60 centimeters in length.

Figure 5:
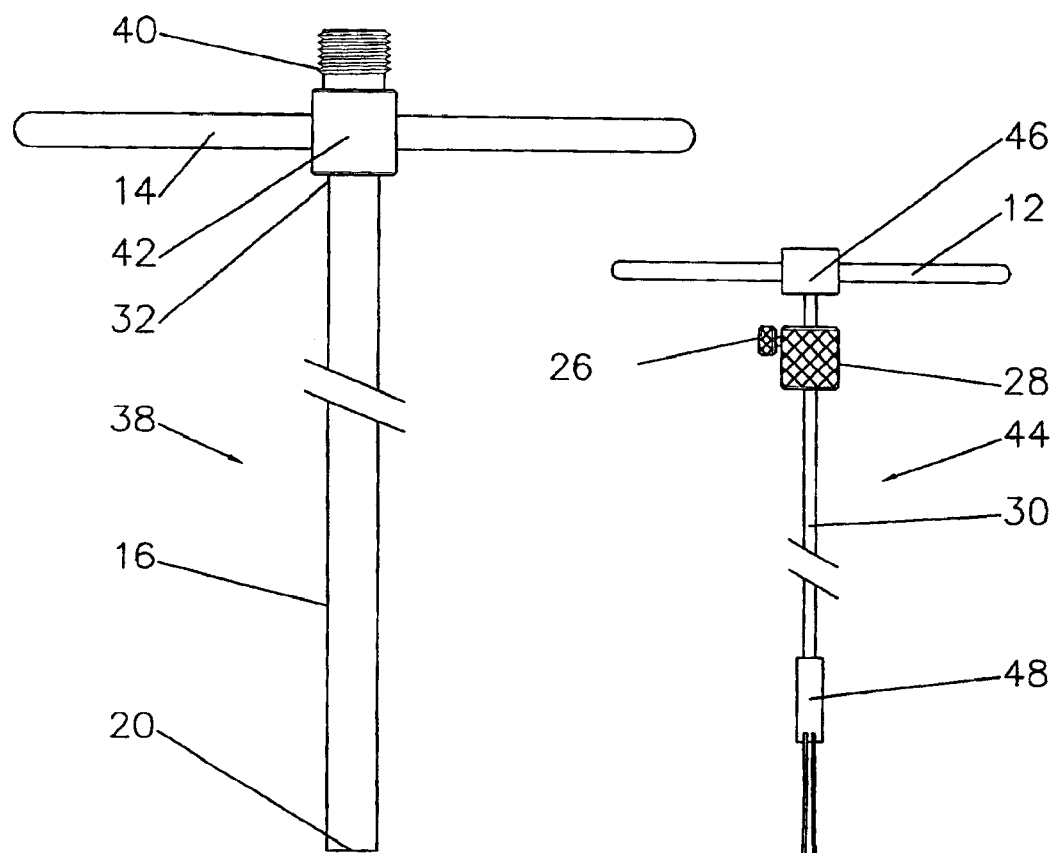
FIG. 5 is a plan view of a laparoscopic lifter apparatus tubular rod component.
Figure 6:
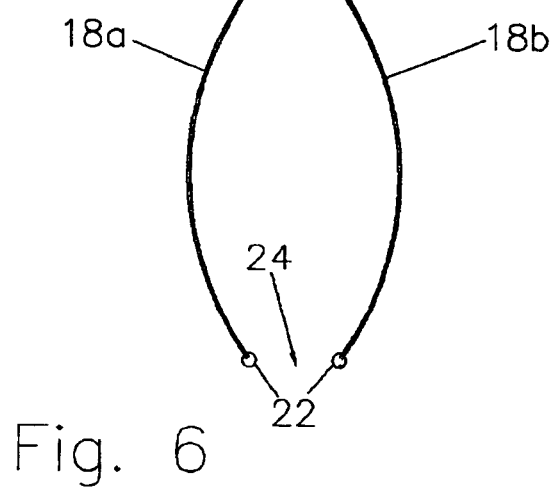
FIG. 6 is a plan view of a laparoscopic lifter apparatus flexible arms component.

The entire organ lifter apparatus 10 can be constructed from 300 series stainless steel. The preformed arcuate arms 18a, 18b can be made from 302 spring temper stainless steel with memory properties so that arms 18a, 18b continually express the same arcuate shapes when extended after many repeated retractions into tubular rod 16. For a disposable organ elevator 10, plastic construction materials can be used. FIGS. 5 and 6 illustrate the laparoscopic organ lifter apparatus 10 components that comprise the organ lifter apparatus 10 when fully assembled and ready for use. FIG. 5 depicts a tubular rod component 38 of the organ lifter apparatus 10 showing a hollow externally threaded coupler 40 adhered to a central hollow knob 42 securing tubular rod 16 substantially perpendicular to second bilateral handle 14. A flexible arms component 44 as illustrated in FIG. 6 is comprised of first bilateral handle 12 having a central element 46 for securing solid rod 30 substantially perpendicular to first bilateral handle 12, the solid rod 30 terminating in connector piece 48 having slot means for griping arms 18a, 18b. Rivet or screw means can also adjoin connector piece 48 to griping arms 18a, 18b. The solid rod 30 passes through ring 28 housing locking screw 26. The tubular rod component 38 and the flexible arms component 44 are assembled to comprise the organ elevator apparatus 10 when the flexible arms component 44 led by flexible arms 18a, 18b is pushed through the tubular rod component 38 hollow externally threaded coupler 40 into the hollow knob 42 and then the tubular rod 16 so that arms 18a, 18b extend out of the tubular rod 16 distal end 20 and assume arcuate shapes. The hollow externally threaded coupler 40 is inserted into the internally threaded ring 28 and affixed by screw means. Locking screw 26 is passes through ring 28 and is tightened to engage solid rod 30 when arms 18a, 18b are extended to a desirable length and position for organ lifting and holding. For sterilizing purposes, it is advantageous to separate the organ lifter apparatus 10 into the two separate components 38, 44 where contaminates can easily be accessed and destroyed.

It should be understood that the organ lifter apparatus 10 is equally useful for removal procedures concerning a variety of organs in addition to spleen removal such as kidney, liver and gallbladder removal. Having described the invention, it is to be understood that many embodiments thereof will readily occur to those skilled in the art and, thus, it is not desired to limit the invention to an exact construction and operation as shown and described in the specification and drawings. Therefore, it is intended that all suitable modifications and equivalents fall within the scope and spirit of the invention.

What is claimed is:

1. A laparoscopic lifter apparatus for elevating and positioning internal organs comprising a flexible arms component having more than one band like flexible arm, wherein said band like flexible arms are mirror image, of each other and equal in length, width and depth having a width substantially three to four times greater than a depth, each band like flexible arm ending in a blunt sphere, and each band like flexible arm having a uniform width throughout its length, said band like flexible arms being made of a metal having memory properties wherein said band like flexible arms continually express the same and an infinite number of arcuate shapes defining an oval space when gradually extended after repeated retractions into a rigid tubular rod, said arcuate shapes determined by organ shape and size needs, and said band like flexible arms able to be manipulated in unison by rotating said first bilateral handles along a central axis through a 360 degree range.

2. The laparoscopic lifter apparatus of claim 1 wherein a maximum distance between said band like flexible arms is achieved upon full extension through said rigid tubular rod.

3. The laparoscopic lifter apparatus of claim 1 wherein said blunt spheres are separated by a distance of substantially 4 to 6 centimeters at full ejection.

4. The laparoscopic lifter apparatus of claim 1 wherein said band like flexible arms are retracted into said rigid tubular rod so that said blunt spheres are touching.

5. The laparoscopic lifter apparatus of claim 1 wherein said band like flexible arms have widths just slightly less than a rigid tubular rod inner diameter to prevent band like flexible arms crossover during retraction.

6. A laparoscopic lifter apparatus for elevating and positioning internal organs comprising a flexible arms component having more than one band like flexible arm wherein said band like flexible arms are mirror images of each other and equal in length, width and depth having a width substantially three to four times greater than a depth, each band like flexible arm ending in a blunt sphere, and each band like flexible arm having a uniform width throughout its length, said band like flexible arms being made of a metal having memory properties wherein said band like flexible arms continually express the same and an infinite number of arcuate shapes defining an oval space when gradually extended after repeated retractions into a rigid tubular rod, said arcuate shapes determined by organ shape and size needs, and said band like flexible arms rotatable in unison through a 360 degree range; and a supporting tubular rod component having said rigid tubular rod wherein arcuate shaped band like flexible arms are retracted diminishing said arcuate shape until said band like arms are fully enclosed in said rigid tubular rod to comprise an assembled laparoscopic lifter apparatus ready for incision insertion, organ manipulation and lifting, said rigid tubular rod having an outside diameter designed to fit through a small incision 10 to 11 millimeters in length.

7. The laparoscopic lifter apparatus of claim 6 wherein a maximum distance between said band like flexible arms is achieved upon full extension through said rigid tubular rod.

8. The laparoscopic lifter apparatus of claim 6 wherein said blunt spheres are separated by a distance of substantially 4 to 6 centimeters at full ejection.

9. The laparoscopic lifter apparatus of claim 6 wherein said band like flexible arms are retracted into said rigid tubular rod so that said blunt spheres are touching.

10. The laparoscopic lifter apparatus of claim 6 wherein said band like flexible arms have widths just slightly less than a rigid tubular rod inner diameter to prevent band like flexible arms crossover during retraction.

11. The laparoscopic lifter apparatus of claim 6 wherein said flexible arms component and said tubular rod component are separated for sterilizing purposes.

12. A method for using said assembled laparoscopic lifter apparatus as described in claim 9 comprising the steps of inserting said tubular rod containing said band like flexible arms into said 10 to 11 millimeter incision, slowly ejecting said band like flexible arms to define an optimal oval space and blunt end opening for selected organ lifting, rotating said band like flexible arms within a 360 degree range and slipping said blunt end opening over an organ end, sliding said band like flexible arms around and then under an organ, resting said organ on said band like flexible arms depth side, performing necessary organ procedures, fully extending said band like flexible arms to achieve a maximum blunt sphere opening, sliding said laparoscopic lifter apparatus away from said organ, retracting said band like flexible arms fully into said rigid tubular rod, removing said laparoscopic lifter from an abdominal cavity.

* * * * *